(12) United States Patent
Kell

(10) Patent No.: US 9,703,090 B2
(45) Date of Patent: Jul. 11, 2017

(54) BOROSCOPE AND A METHOD OF PROCESSING A COMPONENT WITHIN AN ASSEMBLED APPARATUS USING A BOROSCOPE

(71) Applicant: ROLLS-ROYCE PLC, London (GB)

(72) Inventor: James Kell, Nottingham (GB)

(73) Assignee: ROLLS-ROYCE plc, London (GB)

( * ) Notice: Subject to any disclaimer, the term of this patent is extended or adjusted under 35 U.S.C. 154(b) by 232 days.

(21) Appl. No.: 14/675,987

(22) Filed: Apr. 1, 2015

(65) Prior Publication Data

US 2015/0309302 A1     Oct. 29, 2015

(30) Foreign Application Priority Data

Apr. 24, 2014  (GB) .................................. 1407188.0

(51) Int. Cl.
*G02B 23/24* (2006.01)
*B23K 26/03* (2006.01)
(Continued)

(52) U.S. Cl.
CPC ...... *G02B 23/2469* (2013.01); *B23K 26/0066* (2013.01); *B23K 26/0096* (2013.01); *B23K 26/032* (2013.01); *B23K 26/064* (2015.10); *B23K 26/144* (2015.10); *B23K 26/211* (2015.10); *B23K 26/34* (2013.01); *G01N 21/954* (2013.01); *G02B 23/2423* (2013.01);
(Continued)

(58) Field of Classification Search
CPC .......................... G02B 23/2469; G01N 21/954

USPC .................. 250/216, 227.11, 227.24, 227.28
See application file for complete search history.

(56) References Cited

U.S. PATENT DOCUMENTS

| 4,668,088 | A | 5/1987 | Quinque et al. |
| 5,207,673 | A | 5/1993 | Ebling et al. |

(Continued)

FOREIGN PATENT DOCUMENTS

| EP | 0 119 883 A1 | 9/1984 |
| EP | 1 372 016 A2 | 12/2003 |

(Continued)

OTHER PUBLICATIONS

Oct. 23, 2015 Extended Search Report issued in European Patent Application No. 15162163.8.

(Continued)

*Primary Examiner* — Kevin Pyo
(74) *Attorney, Agent, or Firm* — Oliff PLC

(57) ABSTRACT

A boroscope has a first end and a second end and the first end of the boroscope has an optical fiber, a light source, a lens, a beam expander and a transmissive diffractive optical element. The optical fiber extends from the first end of the boroscope to the second end of the boroscope. A laser optical fiber extends from the lens at the first end of the boroscope to the second end of the boroscope and a laser source is arranged to direct a laser beam into the laser optical fiber. The beam expander is provided between the laser optical fiber and the lens and the lens is provided between the beam expander and the transmissive diffractive optical element. The transmissive diffractive optical element is arranged to produce a laser beam with a predetermined shape and a focal length probe extends from the first end of the boroscope.

15 Claims, 3 Drawing Sheets

(51) Int. Cl.
*B23K 26/064* (2014.01)
*G01N 21/954* (2006.01)
*B23K 26/00* (2014.01)
*B23K 26/34* (2014.01)
*B23K 26/144* (2014.01)
*B23K 26/211* (2014.01)
*G02B 27/09* (2006.01)
*F01D 21/00* (2006.01)

(52) U.S. Cl.
CPC ........ *G02B 27/0944* (2013.01); *F01D 21/003* (2013.01); *G01N 2021/9546* (2013.01)

(56) References Cited

U.S. PATENT DOCUMENTS

| | | |
|---|---|---|
| 5,468,238 A | 11/1995 | Mersch |
| 5,780,806 A | 7/1998 | Ferguson et al. |
| 6,759,627 B2 | 7/2004 | Kilburn |
| 7,189,961 B2 * | 3/2007 | Johnston ................ G02B 6/262 250/225 |
| 2004/0074883 A1 | 4/2004 | Kilburn |
| 2006/0042083 A1 | 3/2006 | Baker et al. |
| 2006/0186325 A1 | 8/2006 | Johnston et al. |
| 2007/0035855 A1 * | 2/2007 | Dickensheets ....... A61B 5/0068 359/819 |
| 2010/0238270 A1 | 9/2010 | Bjelkhagen et al. |
| 2011/0248005 A1 | 10/2011 | Briand et al. |
| 2012/0121382 A1 | 5/2012 | Xu et al. |

FOREIGN PATENT DOCUMENTS

| | | |
|---|---|---|
| EP | 1 878 530 A2 | 1/2008 |
| EP | 2 343 148 A1 | 7/2011 |
| EP | 2 345 501 A1 | 7/2011 |
| EP | 2 711 759 A1 | 3/2014 |
| GB | 2 288 906 A | 11/1995 |
| WO | 2013/075954 A1 | 5/2013 |

OTHER PUBLICATIONS

Nov. 9, 2014 Search Report issued in British Application No. 1407188.0.

* cited by examiner

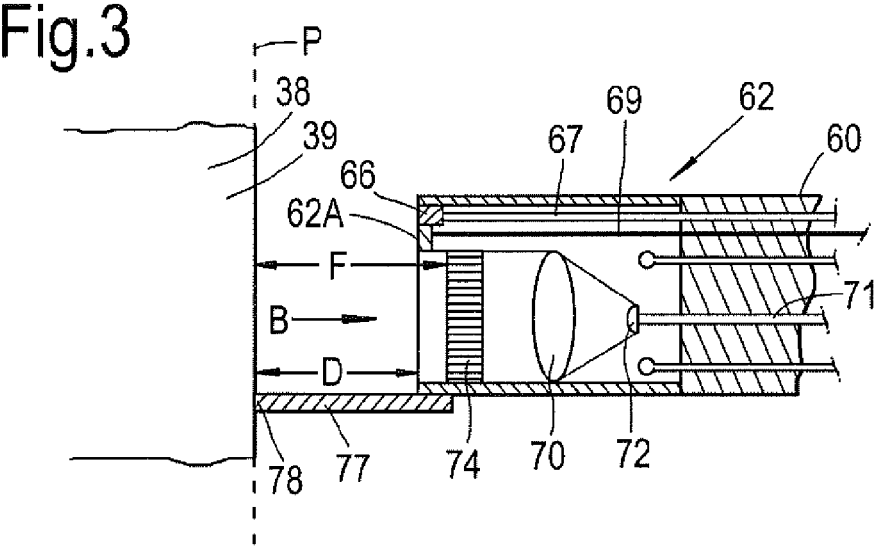
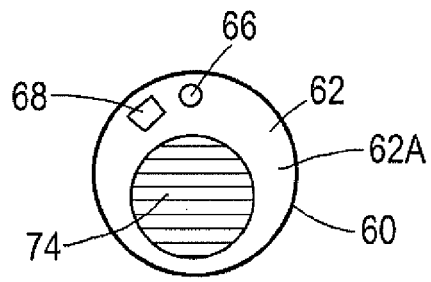
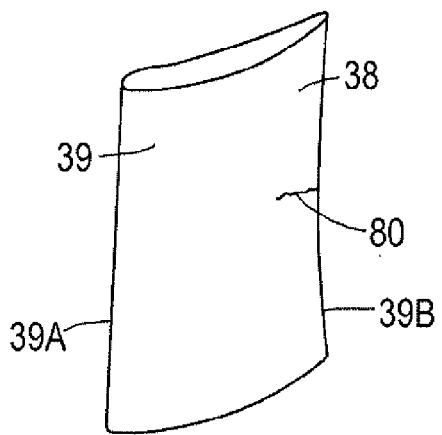
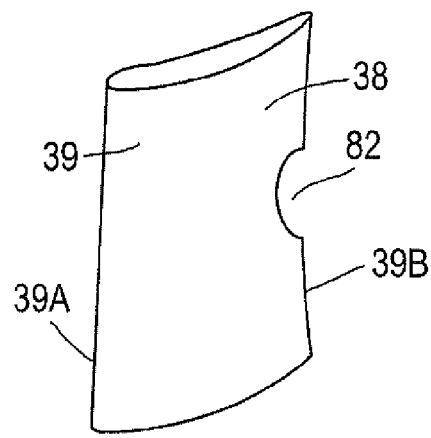
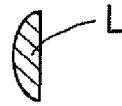

BOROSCOPE AND A METHOD OF PROCESSING A COMPONENT WITHIN AN ASSEMBLED APPARATUS USING A BOROSCOPE

The present invention relates to a boroscope and a method of processing a component within an assembled apparatus in particular relates to a flexible boroscope a method of processing a component within an assembled apparatus using a flexible boroscope.

Currently boroscopes are used to view internal components within an assembled gas turbine engine, or other engine, machine, apparatus etc, to determine if the components within the gas turbine engine are damaged and need repair or if they are undamaged and do not require repair. The use of boroscopes enables the components within the gas turbine engine, or other engine, machine, apparatus etc, to be viewed without having to disassemble the gas turbine engine into modules or sub modules.

There are two types of boroscopes, there are rigid boroscopes and flexible boroscopes. Rigid boroscopes are inserted into an assembled apparatus through an aperture in a casing to enable components within line of sight to be viewed. Flexible boroscopes are also inserted into an assembled apparatus through an aperture in the casing and the boroscope may be continuously inserted and manoeuvred so that components deeper within the apparatus, and not within line of sight, of the aperture may be viewed.

The flexible boroscopes are manoeuvred, or controlled, using cables within the boroscope which are pulled by motors in the control unit of the flexible boroscope.

Some flexible boroscopes are provided with a lens at the remote end of the boroscope and an optical fibre extends through the boroscope to the lens and a laser is provided to supply a laser beam through the optical fibre to the lens so that the lens may focus the laser beam on a component to laser process the component.

However, it is difficult to laser process a component within an assembled apparatus because it is difficult to move the remote end of the boroscope such that the laser beam provides adequate laser processing of the component. In particular because, as mentioned previously, the flexible boroscopes are manoeuvred, or controlled, using cables pulled by the motors in the control unit the remote end of the boroscope cannot be moved at the required speed, with the required accuracy and with the required repeatability. The cables and motors are adequate for positioning a remote end of a boroscope which is used only for viewing components within an assembled apparatus but are not suitable for controlling a remote end of a boroscope which is used for laser processing components within an assembled apparatus.

Accordingly the present disclosure seeks to provide a novel boroscope which reduces, preferably overcomes, the above mention problem(s).

Accordingly the present disclosure provides a boroscope having a first end and a second end, the first end of the boroscope has an optical fibre, a light source, a lens and a transmissive diffractive optical element, the optical fibre extends from the first end of the boroscope to the second end of the boroscope, a laser optical fibre extends from the lens at the first end of the boroscope to the second end of the boroscope, a laser source is arranged to direct a laser beam into the laser optical fibre, the lens is provided between the optical fibre and the transmissive diffractive optical element, the transmissive diffractive optical element is arranged to produce a laser beam with a predetermined shape and a focal length probe extending from the first end of the boroscope.

A remote end of the focal length probe may be arranged in the focal plane of the transmissive diffusive optical element.

The first end of the boroscope has a beam expander, the beam expander is provided between the laser optical fibre and the lens and the lens is provided between the beam expander and the transmissive diffractive optical element.

The transmissive diffractive optical element may be arranged to produce a laser beam with the outline of the shape defined by a straight line and an arcuate line.

The transmissive diffractive optical element may be arranged to produce a laser beam with a half circle shape.

The transmissive diffractive optical element may be arranged to produce a laser beam with a circular, a part-circular, an elliptical, a part-elliptical, a rectangular or a square shape.

The transmissive diffractive optical element may be arranged to produce a laser beam with uniform intensity.

The transmissive diffractive optical element may be arranged to produce an annular intensity distribution, a line that has intensity peaks at its edges, a line that has an intensity peak at one end which gradually reduces in intensity to the other end or a line that has intensity peaks at both ends.

The present disclosure also provides a method of processing a component within an assembled apparatus, the apparatus comprising a casing enclosing the component, the casing having at least one aperture extending there-through, the method comprising: — a) inserting a boroscope through the aperture, the boroscope having a first end and a second end, the first end of the boroscope has an optical fibre, a light source, a lens and a transmissive diffractive optical element, the optical fibre extends from the first end of the boroscope to the second end of the boroscope, a laser optical fibre extends from the lens at the first end of the boroscope to the second end of the boroscope, a laser source is arranged to direct a laser beam into the laser optical fibre, the lens is provided between the optical fibre and the transmissive diffractive optical element, the transmissive diffractive optical element is arranged to produce a laser beam with a predetermined shape and a focal length probe extending from the first end of the boroscope, b) viewing the assembled apparatus within the casing using the optical fibre, c) viewing the assembled apparatus within the casing using the optical fibre while moving the working head of the boroscope to a predetermined position on the component, d) contacting the component with the focal length probe and maintaining the focal length probe in contact with the component, e) supplying a laser beam through the laser optical fibre to the lens, f) directing a laser beam with a predetermined shape onto the surface of the component to process a region of the surface of the component with the predetermined shape, and g) viewing the component with the optical fibre to monitor the processing of the component.

A remote end of the focal length probe may be arranged in the focal plane of the transmissive diffusive optical element.

Step f) may comprise cleaning the surface of the component.

Step f) may comprise ablating the surface of the component.

Step f) may comprise unblocking a cooling aperture.

Step f) may comprise supplying material onto the region of the surface of the component to rebuild the component.

The transmissive diffractive optical element may be arranged to produce a laser beam with the outline of the shape defined by a straight line and an arcuate line.

The transmissive diffractive optical element may be arranged to produce a laser beam with a half circle shape.

The transmissive diffractive optical element may be arranged to produce a laser beam with a circular, a part-circular, an elliptical, a part-elliptical, a rectangular or a square shape.

The transmissive diffractive optical element may be arranged to produce an annular intensity distribution, a line that has intensity peaks at its edges, a line that has an intensity peak at one end which gradually reduces in intensity to the other end or a line that has intensity peaks at both ends.

The assembled apparatus may comprise a gas turbine engine. The component may comprise a compressor blade, a compressor vane, a turbine blade or a turbine vane.

The component may comprise an abradable liner. The abradable liner may be on a casing located around a stage of turbine blades or a stage of compressor blades.

The present invention will be more fully described by way of example with reference to the accompanying drawings, in which:

FIG. 3 is a further enlarged cross-sectional view of the first end of the boroscope shown in FIG. 2.

FIG. 4 is a view in the direction of arrow B in FIG. 3 showing the first end of the boroscope.

FIG. 6 is an enlarged view showing a component before processing according to the present disclosure.

FIG. 7 is an enlarged view showing a component after processing according to the present disclosure.

FIG. 8 is an illustration of a laser beam with a predetermined shape used for processing the component shown in FIG. 6.

Figure 1:
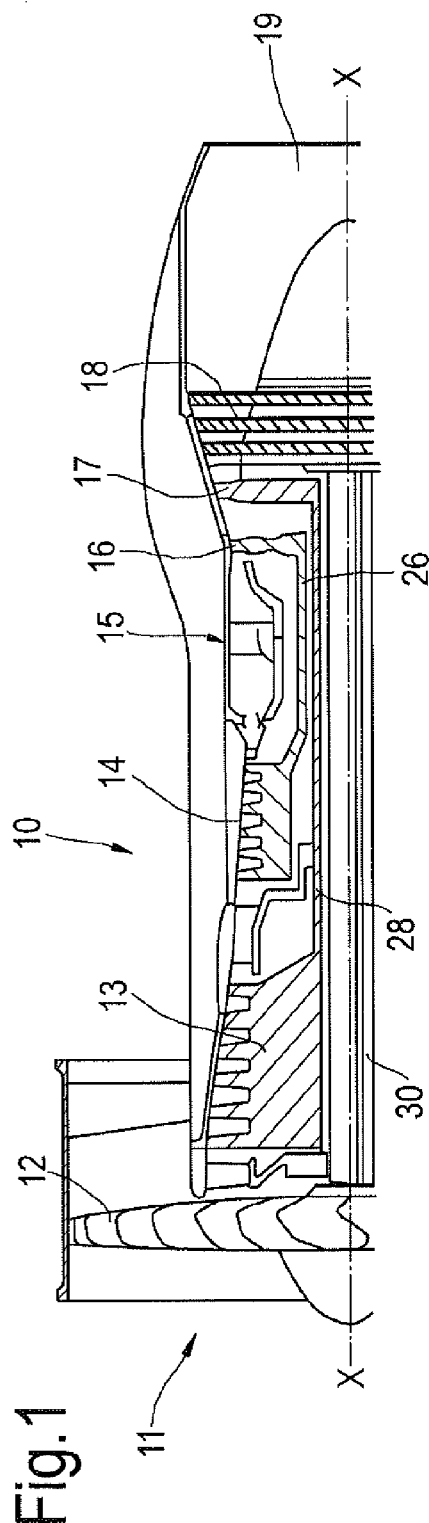
FIG. 1 is cut-away view of a turbofan gas turbine engine.

A turbofan gas turbine engine 10, as shown in FIG. 1, comprises in flow series an intake 11, a fan 12, an intermediate pressure compressor 13, a high pressure compressor 14, a combustor 15, a high pressure turbine 16, an intermediate pressure turbine 17, a low pressure turbine 18 and an exhaust 19. The high pressure turbine 16 is arranged to drive the high pressure compressor 14 via a first shaft 26. The intermediate pressure turbine 17 is arranged to drive the intermediate pressure compressor 13 via a second shaft 28 and the low pressure turbine 18 is arranged to drive the fan 12 via a third shaft 30. In operation air flows into the intake 11 and is compressed by the fan 12. A first portion of the air flows through, and is compressed by, the intermediate pressure compressor 13 and the high pressure compressor 14 and is supplied to the combustor 15. Fuel is injected into the combustor 15 and is burnt in the air to produce hot exhaust gases which flow through, and drive, the high pressure turbine 16, the intermediate pressure turbine 17 and the low pressure turbine 18. The hot exhaust gases leaving the low pressure turbine 18 flow through the exhaust 19 to provide propulsive thrust. A second portion of the air bypasses the main engine to provide propulsive thrust.

Figure 2:
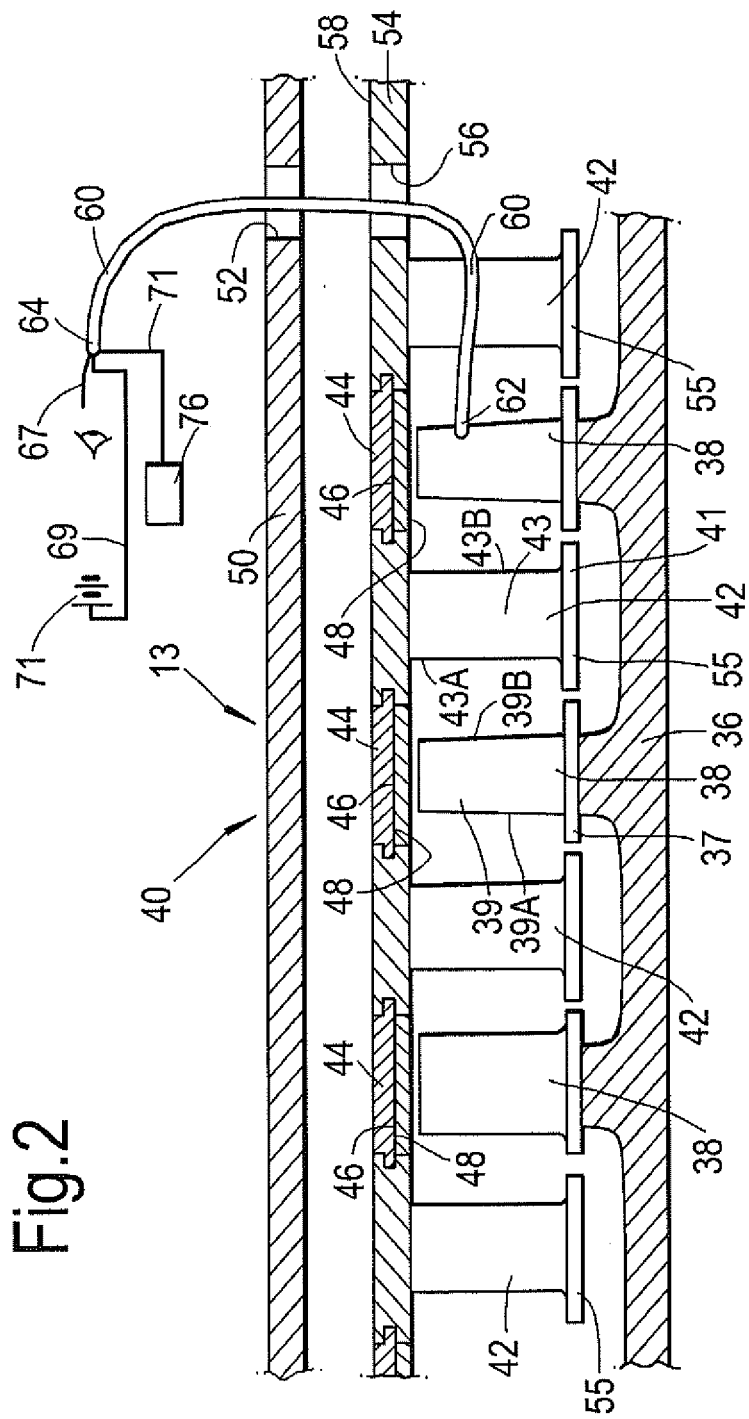
FIG. 2 is an enlarged cross-sectional view through a compressor of the turbofan gas turbine engine showing a boroscope being used in a method of processing a component according to the present disclosure.

The intermediate pressure compressor 13, as shown more clearly in FIG. 2, comprises a rotor 36 carrying a plurality of stages of compressor rotor blades 38 and a stator 40 carrying a plurality of stages of compressor stator vanes 42. The compressor rotor blades 38 in each stage are circumferentially spaced and extend generally radially outwardly from the rotor 36. Each compressor rotor blade 38 comprises a platform 37 and an aerofoil 39 which has a leading edge 39A and a trailing edge 39B. The compressor stator vanes 42 in each stage are circumferentially spaced and extend generally radially inwardly from the stator 40. Each compressor stator vane 42 comprises a platform 41 and an aerofoil 43 which has a leading edge 43A and a trailing edge 43B. The stator 40 also comprises a plurality of shrouds 44 axially interconnecting the stages of compressor stator vanes 42 and the shrouds 44 are positioned radially around a corresponding one of the stages of compressor rotor blades 38. The stator 40 of the intermediate pressure compressor 28 also comprises an outer compressor casing 50 and the outer compressor casing 50 is provided with one or more apertures 52 to allow access for boroscopes and/or repair device. In addition the radially outer platforms 54 of one or more of the compressor stator vanes 42 have one or more apertures 56 to allow access for boroscopes and/or repair devices. The shrouds 44 axially interconnecting the stages of compressor stator vanes 42 form a portion of an inner compressor casing 58. The compressor stator vanes 42 also have radially inner platforms 55. The shrouds 44 positioned around one or more of the compressor rotor blades 38 are provided with an abradable liner, or abradable coating, 48 provided in a recess 46.

A boroscope 60, as shown more clearly in FIGS. 2 to 4, has a first end 62 and a second end 64 and the first end 62 of the boroscope 60 has an end 66 of an optical fibre 67 and a light source 68. The optical fibre 67 in this example extends through the boroscope 60 from the first end 62 of the boroscope 60 to the second end 64 of the boroscope 60. An electrical cable 69 in this example extends through the boroscope 60 from the light source 68 at the first end 62 of the boroscope 60 to the second end 64 of the boroscope 60. An electrical power source 71 is connected to the electrical cable 69 at the second end 64 of the boroscope 60. The boroscope 60 is a flexible boroscope.

The first end 62 of the boroscope 60 also has a lens 70, a beam expander 72 and a transmissive diffractive optical element, a transmissive (DOE), 74. A laser optical fibre 71 extends from the lens 70 at the first end 62 of the boroscope to the second end of the boroscope 64 and in particular the laser optical fibre 71 extends from the beam expander 72 at the first end 62 of the boroscope to the second end of the boroscope 64. A laser source 76 is arranged to direct a laser beam into the laser optical fibre 71 at the second end 64 of the boroscope 60. The beam expander 72 is positioned between the laser optical fibre 71 and the lens 72 and the lens 72 is positioned between the beam expander 72 and the transmissive diffractive optical element 74. The transmissive diffractive optical element 74 is arranged to produce a laser beam L with a predetermined shape.

A focal length probe 77 is secured to and extends from the first end 62 of the boroscope 60. The focal length probe 77 extends in a direction away from the second end 64 of the boroscope 60. The focal length probe 77 is a member which extends from the first end 62 of the boroscope 60 by a distance D and thus the remote end 78 of the focal length probe 77 is spaced a distance D from the first end 62 of the boroscope 60.

The transmissive diffractive optical element 74 is arranged to produce a laser beam L with any suitable, or required, predetermined shape. The transmissive diffractive optical element 74 may produce a laser beam L with uniform intensity over the whole of the predetermined shape. In this particular example the transmissive diffractive optical element 74 is arranged to produce a laser beam L with the outline of the shape defined by a straight line and an arcuate line and more particularly the transmissive diffractive optical element 74 is arranged to produce a laser beam L with a half circle shape, as shown in FIG. 8. The transmissive diffractive optical element 74 has a focal length F. The transmissive diffractive optical element 74 produce a laser beam L with uniform intensity over the whole of the predetermined shape, e.g. half circle shape, in the focal plane P of the transmissive diffractive optical element 74.

It is to be noted that the focal length probe 77 and the transmissive diffractive optical element 74 are arranged relative to each other so that the focal length F and the distance D are arranged at the same distance from the first end 62 of the boroscope 60. In this particular example the transmissive diffractive optical element 74 is set back from the end surface 62A of the first end 62 of the boroscope 60 and so the distance D and the focal length F are not the same. However, if the transmissive diffractive optical element 74 is arranged flush with the end surface 62A of the first end 62 of the boroscope 60, the distance D and the focal length F are the same. In other words the remote end 78 of the focal length probe 77 is arranged in the focal plane P of the transmissive diffractive optical element 74.

The present disclosure provides a method of processing a component, in this example removing a damaged portion of a component, a compressor rotor blade, 38 within an assembled gas turbine engine 10. The gas turbine engine 10 comprises inner and outer casings 58 and 50 respectively, enclosing the component, compressor rotor blade, 38. The inner and outer casings 58 and 50 have at least one aperture 52, 56 extending there-through.

Figure 5:
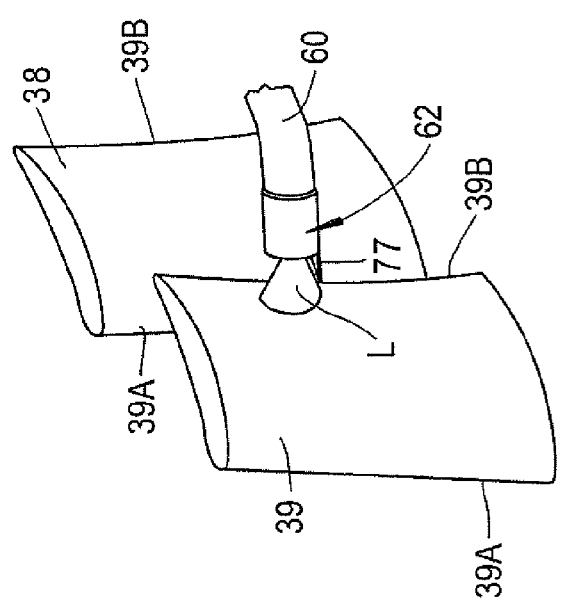
FIG. 5 is a further enlarged view in the direction of arrow A in FIG. 2 showing the first end of the boroscope being used in a method of processing a component according to the present disclosure.

The method comprises inserting the horoscope 60 through the apertures 52, 56, in the outer and inner casings 50 and 58 respectively in particular the first end 62 of the horoscope 60 is inserted. The interior of the intermediate pressure compressor 13 of the assembled gas turbine engine 10 within the casings 50 and 58 is viewed using the end 66 of the optical fibre 67 at the first end 62 of the boroscope 60. The interior of the intermediate pressure compressor 13 of the assembled gas turbine engine 10 within the casings 50 and 58 is viewed while moving the first end 62 of the horoscope 60 to the compressor rotor blade 30 using the end 66 of the optical fibre 67 at the first end 62 of the horoscope 60, as shown in FIGS. 2, 3 and 5. Once the first end 62 of the boroscope 60 is in the correct position, predetermined position, with respect to the component, the compressor rotor blade, 38 as shown in FIG. 5, the first end 62 of the boroscope 60 is moved closer to the component, compressor rotor blade, 38 until the focal length probe 77 contacts the surface of the component, the compressor rotor blade, 38 and the focal length probe 77 is maintained in contact with the surface of the component, compressor rotor blade, 38, as shown in FIG. 3. FIG. 3 shows the remote end 78 of the focal length probe 77 in contact with the surface of the component, the aerofoil 39 of the compressor rotor blade, 38 and the focal plane P of the transmissive diffusive optical element 74 is coincident with the surface of the component 38. The laser source 76 then supplies a laser beam through the laser optical fibre 71 to the lens 70 via the beam expander 72 and the laser beam passes through the lens 70 and into the transmissive diffractive optical element 74. The transmissive diffractive optical element 74 produces a predetermined shape of laser beam L and directs the laser beam onto the surface of the component, aerofoil 39 of the compressor rotor blade, 38 to process a region of the surface of the component, compressor rotor blade, 38 with the predetermined shape. The component is viewed during the processing of the component, compressor rotor blade, 38 via the optical fibre 66 to monitor the processing of the component, compressor rotor blade 38. The boroscope 60 may alternatively or additionally be used to process the platform 37 of the compressor rotor blade 38.

The processing of the surface of the component may simply be cleaning of the surface of the component, e.g. cleaning the surface of the compressor rotor blade 38.

Alternatively, the processing of the component, compressor rotor blade, 38 may be ablating of the surface of the component 38 as is shown in FIGS. 6 and 7. The ablating of the component, compressor rotor blade, 38 may be used to remove a damaged region of the component 38. FIG. 6 shows a crack 80 in the trailing edge 39B of the aerofoil 39 of the compressor rotor blade 38 and FIG. 7 shows the trailing edge 39B of the aerofoil 39 of the compressor rotor blade 38 after ablating to remove a scallop shape from the trailing edge 39B of the aerofoil 39 of the compressor rotor blade 38 and hence remove the damaged, cracked, region of the trailing edge 39B of the aerofoil 39 of the compressor rotor blade 38. FIG. 8 shows the predetermined shape of the laser beam L produced by the transmissive diffractive optical element 74 to produce the scallop shape in the trailing edge 39B of the trailing edge 39 of the compressor rotor blade 38. The boroscope 60 may alternatively or additionally be used to ablate, or remove, a scallop shape from the platform 37 of the compressor rotor blade 38.

Additionally, the processing of the component may be building up, or rebuilding, the surface of the component by supplying material onto a region of the surface of the component and melting the surface of the component and melting the supplied material such that the supplied material fuses with and then builds up on the surface of the component. The material supplied may be the same alloy, e.g. steel, aluminium alloy, titanium alloy, iron superalloy, cobalt superalloy or nickel superalloy, as the alloy of the component or the same ceramic as the ceramic of the component. Thus, the platform 37 and or aerofoil 39 of the compressor rotor blade 38 may be rebuilt.

Similarly, the boroscope 60 may be used to process, e.g. clean, ablate or build up, the compressor stator vane 42. In another example the processing of the component may be rebuilding up the abradable coating 48 in the recess 46 in the shrouds 44 surrounding the compressor rotor blades 38.

The processing of the component may comprise ablating a turbine rotor blade, a turbine stator vane, a combustion chamber wall, a combustion chamber tile or other cooled component. The processing of the component may comprise cleaning a turbine rotor blade, a turbine stator vane, a combustion chamber wall, a combustion chamber tile or other cooled component.

The processing of the component may comprise unblocking a cooling aperture in a turbine rotor blade, a turbine stator vane, a combustion chamber wall, a combustion chamber tile or other cooled component. The unblocking of the cooling aperture may comprise ablating of the blockage in the cooling aperture.

The processing of the component may comprise supplying material onto the region of the surface of the component to rebuild the component.

The different laser processing is achieved by adjusting the power density of the laser beam and/or the interaction time of the laser beam with the component. Power densities of greater than $10^9$ W/mm$^2$ for interaction times of about $10^{-8}$ s produce vapourisation, or ablation, whereas power densities of less than $10^7$ W/mm$^2$ for interaction times of about $10^{-8}$ s produce heating and power densities between $10^9$ W/mm$^2$ and $10^7$ W/mm$^2$ for interaction times of about $10^{-8}$ s produce melting. Power densities of greater than $10^7$ W/mm$^2$ for interaction times of about $10^4$ s produce vapourisation, or ablation, whereas power densities of less than $10^4$ W/mm$^2$ for interaction times of about $10^{-4}$ s produce heating and power densities between $10^7$ W/mm$^2$ and $14^7$ W/mm$^2$ for interaction times of about $10^{-4}$ s produce melting.

Power densities of greater than $10^5$ W/mm$^2$ for interaction times of about 1 s produce vapourisation, or ablation, whereas power densities of less than $10^5$ W/mm$^2$ for interaction times of about 1 s produce melting.

Although the present disclosure has referred to the transmissive diffractive optical element producing a half circular predetermined shape of laser beam it is equally possible to use any other suitable predetermined shape of laser beam for example circular, part-circular, elliptical, part-elliptical, rectangular, square etc. The transmissive diffractive optical element produces a laser beam with a uniform intensity for each of these shapes.

Although the present disclosure has referred to the transmissive diffractive optical element producing a laser beam with uniform intensity, the transmissive diffractive optical element may be arranged to produce other suitable intensity distributions. For example the transmissive diffractive optical element may produce an annular intensity distribution, a line that has intensity peaks at its edges, a line that has an intensity peak at one end which gradually reduces in intensity to the other end or a line that has intensity peaks at both ends to account for thermal conduction in between.

The present disclosure may be used to clean the surface of any other component in an assembled apparatus, e.g. an oil rig, a steam turbine, a turbomachine, a ship engine, a nuclear reactor, an internal combustion engine, an aircraft, a ship, a locomotive etc.

The present disclosure may be used to ablate the surface of any other component in an assembled apparatus, e.g. an oil rig, a steam turbine, a turbomachine, a ship engine, a nuclear reactor, an internal combustion engine, an aircraft, a ship, a locomotive etc.

The present disclosure may be used to build up the surface of any other component in an assembled apparatus, e.g. an oil rig, a steam turbine, a turbomachine, a ship engine, a nuclear reactor, an internal combustion engine, an aircraft, a ship, a locomotive etc.

An advantage of the boroscope according to the present disclosure is that the transmissive diffractive optical element produces a shaped laser beam and there is no need to move the first end of the boroscope during the processing of the component. The focal length probe ensures that the transmissive diffractive optical element is focussed on the surface of the component allowing maximum efficiency of processing of the component, e.g. maximum cleaning, maximum ablating etc and ensures that the processing is within a prescribed operating window. The transmissive diffractive optical element has a small, or short, depth of filed, this ensures that the laser beam expands significantly beyond the focal plane of the transmissive diffractive optical element, and this reduces the risk of collateral damage to surrounding components once the component has been ablated.

The invention claimed is:

1. A boroscope having a first end and a second end, the first end of the boroscope has an optical fibre, a light source, a lens and a transmissive diffractive optical element, the optical fibre extends from the first end of the boroscope to the second end of the boroscope, a laser optical fibre extends from the lens at the first end of the boroscope to the second end of the boroscope, a laser source is arranged to direct a laser beam into the laser optical fibre, the lens is provided between the laser optical fibre and the transmissive diffractive optical element, the transmissive diffractive optical element is arranged to produce a laser beam with a predetermined shape and a focal length probe extending from the first end of the boroscope,
wherein the transmissive diffractive optical element is arranged to produce a laser beam with the outline of the shape defined by a straight line and an arcuate line.

2. The boroscope as claimed in claim 1, wherein the first end of the boroscope has a beam expander, the beam expander is provided between the laser optical fibre and the lens and the lens is provided between the beam expander and the transmissive diffractive optical element.

3. The boroscope as claimed in claim 1, wherein the transmissive diffractive optical element is arranged to produce a laser beam with a shape selected from the group consisting of a half circular shape, a part-circular shape, and a part-elliptical shape.

4. The boroscope as claimed in claim 1, wherein the transmissive diffractive optical element is arranged to produce a laser beam with uniform intensity.

5. A method of processing a component within an assembled apparatus, the apparatus comprising a casing enclosing the component, the casing having at least one aperture extending there-through, the method comprising:
a) inserting a boroscope through the aperture, the boroscope having a first end and a second end, the first end of the boroscope has an optical fibre, a light source, a lens and a transmissive diffractive optical element, the optical fibre extends from the first end of the boroscope to the second end of the boroscope, a laser optical fibre extends from the lens at the first end of the boroscope to the second end of the boroscope, a laser source is arranged to direct a laser beam into the laser optical fibre, the lens is provided between the laser optical fibre and the transmissive diffractive optical element, the transmissive diffractive optical element is arranged to produce a laser beam with a predetermined shape and a focal length probe extending from the first end of the boroscope,
b) viewing the assembled apparatus within the casing using the optical fibre,
c) viewing the assembled apparatus within the casing using the optical fibre while moving the working head of the boroscope to a predetermined position on the component,
d) contacting the component with the focal length probe and maintaining the focal length probe in contact with the component,
e) supplying a laser beam through the laser optical fibre to the lens,
f) directing a laser beam with a predetermined shape onto the surface of the component to process a region of the surface of the component with the predetermined shape, and g) viewing the component with the optical fibre to monitor the processing of the component,
wherein the transmissive diffractive optical element is arranged to produce a laser beam with the outline of the shape defined by a straight line and an arcuate line.

6. The method as claimed in claim 5, wherein step f) comprises cleaning the surface of the component.

7. The method as claimed in claim 5, wherein step f) comprises ablating the surface of the component.

8. The method as claimed in claim 5, wherein step f) comprises unblocking a cooling aperture.

9. The method as claimed in claim 5, wherein step f) comprises supplying material onto the region of the surface of the component to rebuild the component.

10. The method as claimed in claim 5, wherein the transmissive diffractive optical element is arranged to produce a laser beam with a shape selected from the group consisting of a half circular shape, a part-circular shape, and a part-elliptical shape.

11. The method as claimed in claim 5, wherein the transmissive diffractive optical element is arranged to produce a laser beam with uniform intensity.

12. The method as claimed in claim 5, wherein the assembled apparatus comprises a gas turbine engine.

13. The method as claimed in claim 12, wherein the component is selected from the group consisting of a compressor blade, a compressor vane, a turbine blade and a turbine vane.

14. The method as claimed in claim 12, wherein the component comprises an abradable liner.

15. The method as claimed in claim 14, wherein the abradable liner is on a casing located around a stage of blades, the blades are selected from the group consisting of turbine blades and compressor blades.

* * * * *